United States Patent
Bae et al.

(10) Patent No.: US 9,899,039 B2
(45) Date of Patent: *Feb. 20, 2018

(54) METHOD FOR DETERMINING ALCOHOL CONSUMPTION, AND RECORDING MEDIUM AND TERMINAL FOR CARRYING OUT SAME

(71) Applicant: Foundation of Soongsil University—Industry Cooperation, Seoul (KR)

(72) Inventors: Myung Jin Bae, Seoul (KR); Sang Gil Lee, Busan (KR); Geum Ran Baek, Seoul (KR)

(73) Assignee: FOUNDATION OF SOONGSIL UNIVERSITY-INDUSTRY COOPERATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/113,743

(22) PCT Filed: Jan. 24, 2014

(86) PCT No.: PCT/KR2014/000727
§ 371 (c)(1),
(2) Date: Jul. 22, 2016

(87) PCT Pub. No.: WO2015/111772
PCT Pub. Date: Jul. 30, 2015

(65) Prior Publication Data
US 2017/0032804 A1 Feb. 2, 2017

(30) Foreign Application Priority Data
Jan. 24, 2014 (KR) ........................ 10-2014-0008742

(51) Int. Cl.
*G10L 25/66* (2013.01)
*G10L 15/16* (2006.01)
(Continued)

(52) U.S. Cl.
CPC ................ *G10L 25/66* (2013.01); *A61B 5/18* (2013.01); *A61B 5/4803* (2013.01);
(Continued)

(58) Field of Classification Search
None
See application file for complete search history.

(56) References Cited

U.S. PATENT DOCUMENTS

| 5,776,055 A | 7/1998 | Hayre |
| 5,913,188 A * | 6/1999 | Tzirkel-Hancock .... G10L 15/02 704/221 |

(Continued)

FOREIGN PATENT DOCUMENTS

| EP | 1850328 A1 | 10/2007 |
| JP | 2003-36087 A | 2/2003 |

(Continued)

OTHER PUBLICATIONS

Kim (Kim, Jonathan, Hrishikesh Rao, and Mark Clements. "Investigating the use of formant based features for detection of affective dimensions in speech." Affective computing and intelligent interaction (2011): 369-377.).*

(Continued)

*Primary Examiner* — Pierre-Louis Desir
*Assistant Examiner* — Jonathan Kim
(74) *Attorney, Agent, or Firm* — Sang Ho Lee; Novick, Kim & Lee, PLLC

(57) ABSTRACT

Disclosed is a method for determining alcohol consumption capable of analyzing alcohol consumption in a time domain by analyzing a formant slope of a voice signal, and a (Continued)

recording medium and a terminal for carrying out same. An terminal for determining whether a person is drunk comprises: a voice input unit for generating a voice frame by receiving a voice signal; a voiced/unvoiced sound analysis unit for determining whether a received voiced frame corresponds to a voiced sound; a formant frequency extraction unit for extracting a plurality of formant frequencies of the voice frame corresponding to the voiced sound; and an alcohol consumption determining unit for calculating a formant slope between the plurality of formant frequencies, and determining the state of alcohol consumption depending on the formant slope, thereby determining whether a person is drunk by analyzing the formant slope of an inputted voice.

18 Claims, 4 Drawing Sheets

(51) Int. Cl.
| | |
|---|---|
| G10L 25/93 | (2013.01) |
| G10L 25/15 | (2013.01) |
| A61B 5/18 | (2006.01) |
| A61B 5/00 | (2006.01) |
| G10L 19/12 | (2013.01) |
| A61B 10/00 | (2006.01) |
| G10L 25/30 | (2013.01) |

(52) U.S. Cl.
CPC ............ *A61B 5/4845* (2013.01); *G10L 15/16* (2013.01); *G10L 19/12* (2013.01); *G10L 25/15* (2013.01); *G10L 25/93* (2013.01); *A61B 2010/0009* (2013.01); *A61B 2503/22* (2013.01); *G10L 25/30* (2013.01)

(56) References Cited

U.S. PATENT DOCUMENTS

| | | | | |
|---|---|---|---|---|
| 5,983,189 A * | 11/1999 | Lee | ............... | G08B 21/06 704/273 |
| 6,006,188 A * | 12/1999 | Bogdashevsky | ......... | G10L 17/26 704/270 |
| 6,205,420 B1 * | 3/2001 | Takagi | ............... | G10L 21/04 704/200 |
| 6,275,806 B1 * | 8/2001 | Pertrushin | ............... | G10L 17/26 704/270 |
| 6,446,038 B1 * | 9/2002 | Bayya | ............... | G10L 25/69 704/231 |
| 6,748,301 B1 | 6/2004 | Ryu | | |
| 8,478,596 B2 | 11/2005 | Schultz | | |
| 7,925,508 B1 | 4/2011 | Michaelis | | |
| 7,962,342 B1 | 6/2011 | Coughlan et al. | | |
| 8,938,390 B2 * | 1/2015 | Xu | ............... | A61B 5/7264 704/231 |
| 9,058,816 B2 * | 6/2015 | Lech | ............... | G10L 17/26 |
| 9,659,571 B2 * | 5/2017 | Van Der Schaar | ...... | G08B 3/10 |
| 9,672,809 B2 | 6/2017 | Togawa et al. | | |
| 2002/0010587 A1 * | 1/2002 | Pertrushin | ............... | G10L 17/26 704/275 |
| 2002/0194002 A1 * | 12/2002 | Petrushin | ............... | G10L 17/26 704/270 |
| 2003/0069728 A1 * | 4/2003 | Tato | ............... | G10L 17/26 704/231 |
| 2004/0167774 A1 * | 8/2004 | Shrivastav | ............... | G10L 17/26 704/207 |
| 2005/0075864 A1 * | 4/2005 | Kim | ............... | G10L 25/48 704/206 |
| 2005/0102135 A1 * | 5/2005 | Goronzy | ............... | G10L 15/00 704/213 |
| 2007/0071206 A1 * | 3/2007 | Gainsboro | ............... | H04M 3/2281 379/168 |
| 2007/0124135 A1 | 5/2007 | Schultz | | |
| 2007/0192088 A1 * | 8/2007 | Oh | ............... | G10L 15/02 704/209 |
| 2007/0213981 A1 * | 9/2007 | Meyerhoff | ............... | G10L 17/26 704/243 |
| 2007/0288236 A1 * | 12/2007 | Kim | ............... | G10L 25/93 704/231 |
| 2009/0265170 A1 | 10/2009 | Irie et al. | | |
| 2010/0010689 A1 | 1/2010 | Yasushi et al. | | |
| 2011/0035213 A1 | 2/2011 | Malenovsky | | |
| 2011/0282666 A1 | 11/2011 | Washio | | |
| 2012/0089396 A1 * | 4/2012 | Patel | ............... | G10L 25/00 704/249 |
| 2012/0116186 A1 * | 5/2012 | Shrivastav | ............... | A61B 5/0507 600/301 |
| 2012/0262296 A1 * | 10/2012 | Bezar | ............... | G10L 17/26 340/573.1 |
| 2013/0006630 A1 * | 1/2013 | Hayakawa | ............... | G10L 17/26 704/239 |
| 2013/0253933 A1 | 9/2013 | Maruta | | |
| 2014/0122063 A1 * | 5/2014 | Gomez Vilda | ......... | G10L 19/02 704/200.1 |
| 2014/0188006 A1 * | 7/2014 | Alshaer | ............... | A61B 5/7282 600/586 |
| 2014/0379348 A1 * | 12/2014 | Sung | ............... | G10L 25/75 704/254 |
| 2015/0127343 A1 | 5/2015 | Mullor et al. | | |
| 2015/0257681 A1 | 9/2015 | Shuster et al. | | |
| 2015/0310878 A1 * | 10/2015 | Bronakowski | ......... | G10L 25/63 704/246 |
| 2015/0351663 A1 | 12/2015 | Zigel | | |
| 2016/0155456 A1 * | 6/2016 | Wang | ............... | G10L 25/81 704/208 |
| 2016/0379669 A1 | 12/2016 | Bae et al. | | |
| 2017/0004848 A1 | 1/2017 | Bae et al. | | |

FOREIGN PATENT DOCUMENTS

| | | |
|---|---|---|
| JP | 2010-015027 A | 1/2010 |
| JP | 5017534 B2 | 9/2012 |
| KR | 10-1997-0038004 A | 7/1997 |
| KR | 10-0201256 B1 | 6/1999 |
| KR | 10-0206205 B1 | 7/1999 |
| KR | 1999-0058415 A | 7/1999 |
| KR | 10-2004-0033783 A | 4/2004 |
| KR | 10-0497837 B1 | 6/2005 |
| KR | 10-0664271 B1 | 1/2007 |
| KR | 10-2009-0083070 A | 8/2009 |
| KR | 10-2012-0074314 A | 7/2012 |
| WO | 2012/014301 A1 | 2/2012 |

OTHER PUBLICATIONS

Broad (Broad, David J., and Frantz Clermont. "Formant estimation by linear transformation of the LPC cepstrum." The Journal of the Acoustical Society of America 86.5 (1989)).*

Sato (Sato, Nobuo, and Yasunari Obuchi. "Emotion recognition using mel-frequency cepstral coefficients." Information and Media Technologies 2.3 (2007): 835-848.).*

Kim, Jonathan, Hrishikesh Rao, and Mark Clements. "Investigating the use of formant based features for detection of affective dimensions in speech." Affective computing and intelligent interaction (2011): 369-377.*

Geumran Baek et al. "A Study on Voice Sobriety Test Algorithm in a Time-Frequency Domain" International Journal of Multimedia and Ubiquitous Engineering vol. 8 No. 5 (2013), pp. 365-402.

Chan Joong Jung et al. "Speech Sobriety Test Based on Formant Energy Distribution" International Journal of Multimedia and Ubiquitous Engineering vol. 8 No. 6 (2013), pp. 209-216.

Geumran Baek et al. "A Study on Judgment of Intoxication State Using Speech," Information and Telecommunication Department, Soongsil University, pp. 277-282.

Seong-Geon Bae et al. "A Study on Personalized Frequency Bandwidth of Speech Signal using Formant to LPC," The Journal of Korean Institute of Communications and Information Sciences (winter), 2013, pp. 669-670.

(56) References Cited

OTHER PUBLICATIONS

Seong-Geon Bae et al. "A Study on Drinking Judgement Method of Speech Signal Using the Fomant Deviation in be Linear Prediction Coefficient," he Journal of Korean Institute of Communications and Information Sciences (winter), 2013, pp. 667-668.
Lee, Won Hui et al. "Valid-frame Distance Deviation of Drunk and non-Drunk Speech" The Journal of Korea Information and Communications Society (winter) 2014, pp. 876-877, Jan. 2014.
Jung, Chan Joong et al. "A Study on Detecting Decision Parameter about Drinking in Time Domain," The Journal of Korea Information and Communications Society (winter) 2014, pp. 784-785, Jan. 2013.
Lee, Won-Hee et al.."A Study on Drinking Judgement using Differential Signal in Speech Signal", The Journal of Korea Information and Communications Society (winter) 2014, pp. 878-879, Jan. 2014.
Seong Geon Bae, Dissertation for Ph.D, "A study on Improving Voice Surveillance System Against Drunk Sailing". Information and Communication Engineering Dept., Soongsil University, Republic of Korea. Dec. 2011 (English Abstract at pp. x-xii).
Chan Joong Jung et al. "A Study on Drunken Decision using Spectral Envelope Changes" Korea Institute of Communications and Information Sciences, Winter Conference, vol. 2013 No. 1 (2013), pp. 674-675.
Baumeister, Barbara, Christian Heinrich, and Florian Schiel. "The influence of alcoholic intoxication on the fundamental frequency of female and male speakers." The Journal of the Acoustical Society of America 132.1 (2012): 442-451.
Schuller, Bjorn W., et al. "The INTERSPEECH 2011 Speaker State Challenge." INTERSPEECH. 2011.
Hollien, Harry, et al. "Effects of ethanol intoxication on speech suprasegmentals." The Journal of the Acoustical Society of America 110.6 (2001): 3198-3206.
Tae-Hun Kim et al. "Drinking Speech System", Department of Information Communication, Sang Myung University, Nov. 2016, pp. 257-262.
See-Woo Lee, "A Study on Formant Variation with Drinking and Nondrinking Condition," Department of Information & Telecommunication Engineering, Sangmyung University, vol. 10, No. 4, pp. 805-810, 2009.
Bocklet, Tobias, Korbinian Riedhammer, and Elmar Noth. "Drink and Speak: On the automatic classification of alcohol intoxication by acoustic, prosodic and text-based features." Twelfth Annual Conference of the International Speech Communication Association. 2011.

\* cited by examiner

METHOD FOR DETERMINING ALCOHOL CONSUMPTION, AND RECORDING MEDIUM AND TERMINAL FOR CARRYING OUT SAME

TECHNICAL FIELD

The present invention relates to a method of determining whether alcohol has been consumed using a voice analysis, and a recording medium and terminal for carrying out the same.

BACKGROUND ART

Although there may be differences among individuals, a drunk driving accident is likely to happen when a driver is half-drunk or drunk. As methods of measuring drunkenness, there is a method of measuring the concentration of alcohol within exhaled air during respiration using a breathalyzer equipped with an alcohol sensor and a method of measuring the concentration of alcohol in the blood flow using a laser. Generally, the former method is usually used for cracking down on drunk driving. In this case, when any driver refuses a drunkenness test, the Widmark Equation may be used to estimate a blood alcohol concentration by collecting the blood of the driver with his or her consent.

A technology for determining whether a driver has consumed alcohol and controlled starting device for a vehicle in order to prevent drunk driving is commercialized. Some vehicles to which the technology is applied are already commercially available. Such a technology works by enabling or disabling a vehicle to be started by attaching a detection device equipped with an alcohol sensor to the starting device of the vehicle, this is a field in which much research is being conducted by domestic and foreign automotive manufacturers. These methods use an alcohol sensor and thus may relatively accurately measure a concentration of alcohol. However, in an environment with high humidity and dust, such as an automotive interior environment, the alcohol sensor has a low accuracy and is not entirely usable due to frequent failures. Furthermore, the sensor has a short lifetime. Accordingly, when the sensor is combined to an electronic device, there is an inconvenience of having to repair the electronic device in order to replace the sensor.

DISCLOSURE

Technical Problem

An aspect of the present invention is directed to a method of determining whether a person is drunk after consuming alcohol by analyzing a formant slope of a voice signal, and a recording medium and a terminal for carrying out the same.

Technical Solution

According to an aspect of the present invention, an alcohol consumption determination method includes receiving a voice signal and converting the received voice signal into a plurality of voice frames, extracting a voice frame corresponding to a voiced sound among the plurality of voice frames, extracting a plurality of formant frequencies of the voice frame corresponding to the voiced sound, extracting a formant slope between two formant frequencies among the plurality of formant frequencies, and determining whether alcohol has been consumed according to the formant slope.

The extracting of a plurality of formant frequencies of the voice frame corresponding to the voiced sound may include extracting first to fourth formant frequencies of the voice frame.

The extracting of a formant slope between two formant frequencies among the plurality of formant frequencies may include extracting a formant slope between the first formant frequency and the fourth formant frequency or extracting a formant slope between the second formant frequency and the fourth formant frequency.

The determining of whether alcohol has been consumed according to the formant slope may include counting the number of voice frames each having a formant slope less than a predetermined threshold, calculating a ratio of the counted number of voice frames to the total number of voice frames, and determining that alcohol has been consumed when the calculated ratio is greater than a predetermined value.

According to an embodiment of the present invention, a computer-readable recording medium has a program recorded thereon for performing the above-described alcohol consumption determination method.

According to an embodiment of the present invention, an alcohol consumption determination terminal includes a voice input unit configured to receive a voice signal and generate a voice frame; a voiced/unvoiced sound analysis unit configured to receive the voice frame and determine whether the voice frame corresponds to a voiced sound; a formant frequency extraction unit configured to extract a plurality of formant frequencies of the voice frame corresponding to the voiced sound; and an alcohol consumption determination unit configured to generate formant slopes between the plurality of formant frequencies and determine whether alcohol has been consumed according to the formant slopes.

The alcohol consumption determination unit may include a counting unit configured to compare a formant slope of the voice frame determined as the voiced sound in the entire section of the voice signal with a pre-stored threshold and count the number of voice frames each having a formant slope smaller than the threshold.

The alcohol consumption determination unit may further include a ratio calculation unit configured to compare a result calculated by the counting unit with the total number of voice frames to calculate a ratio therebetween.

The alcohol consumption determination unit may further include a determination unit configured to determine that alcohol has been consumed when the ratio calculated by the ratio calculation unit is greater than a predetermined value.

When the formant slopes between the plurality of formant frequencies are generated, the alcohol consumption determination unit may generate any one of a formant slope between the first formant frequency and the fourth formant frequency among the formant frequencies and a formant slope between the second formant frequency and the fourth formant frequency among the formant frequencies.

Advantageous Effects

As described above, according to an aspect of the present invention, whether alcohol has been consumed may be determined by analyzing a formant slope of an input voice signal.

MODES FOR CARRYING OUT THE INVENTION

Hereinafter, exemplary embodiments of the present invention will be described in detail with reference to the accompanying drawings. In adding reference numbers for elements in each figure, it should be noted that like reference numbers already used to denote like elements in other figures are used for elements wherever possible.

Figure 1:
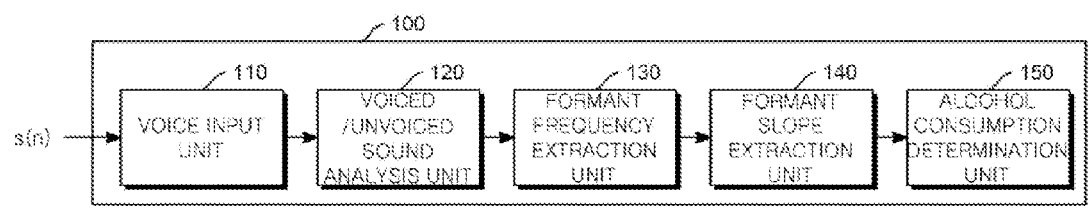
FIG. 1 is a control block diagram of an alcohol consumption determination terminal according to an embodiment of the present invention.

FIG. 1 is a control block diagram of an alcohol consumption determination terminal according to an embodiment of the present invention.

An alcohol consumption determination terminal 100 may include a voice input unit 110, a voiced/unvoiced sound analysis unit 120, a formant frequency extraction unit 130, a formant slope extraction unit 140, and an alcohol consumption determination unit 150.

The voice input unit 110 may receive a person's voice, convert the received voice into voice data, convert the voice data into voice frame data in units of frames, and output the voice frame data. The voice input unit 110 may convert voice signals in the frequency domain using a transform method such as Fast Fourier Transform (FFT).

The voiced/unvoiced sound analysis unit 120 may receive a voice frame, extract predetermined features from the voice frame, and analyze whether the voice frame is associated with a voiced sound, an unvoiced sound, or noise according to the extracted features.

The voiced/unvoiced sound analysis unit 120 may determine whether the voice frame corresponds to a voiced sound, an unvoiced sound, or background noise according to a recognition result obtained by the above method. The voiced/unvoiced sound analysis unit 120 may separate and output the voice frame as a voice sound, an unvoiced sound, or background noise according to a result of the determination.

The formant frequency extraction unit 130 may extract a formant frequency for a voice frame determined as a voice sound through the voiced/unvoiced sound analysis unit 120. The formant frequency is a frequency band peak to which sound energy is concentrated in a spectrogram of an input voice signal. The frequency band with a formant refers to sound energy with relatively high intensity. Accordingly, consonants have no formant frequencies, and only vowels have formant frequencies. The formant frequencies are called F1, F2, F3, F4, and F5 in ascending order of harmonics in a frequency intensity distribution. Typically, for a male adult, about five formant frequencies occur in a range up to 5000 Hz. For a female adult, about four formant frequencies occur (that is, one less than the number of formant frequencies for a male adult).

The formant slope extraction unit 140 finds a formant slope using the formant frequencies extracted by the formant frequency extraction unit 130. The formant slope is a slope of a straight line connecting one formant frequency and another. For example, a slope of a straight line connecting a first formant frequency F1 and a fourth formant frequency F4 may be defined as a formant slope F14.

The alcohol consumption determination unit 150 may determine whether alcohol has been consumed using the formant slope. The frequency after drinking is characterized in that a drunk person cannot speak quickly and thus pronunciation accuracy is reduced. This phenomenon causes a spectrum in the frequency domain to be smoothed. This means that a formant curve with a gentle slope can be obtained in the frequency domain. Thus, the alcohol consumption determination unit 150 may compare the formant slope of the voice frame determined as the voiced sound with a threshold. The alcohol consumption determination unit 150 may determine that alcohol has been consumed when a ratio of the number of voice frames that are determined as having formant slopes smaller than the threshold to the total number of voice frames is greater than or equal to a certain value.

Figure 2:
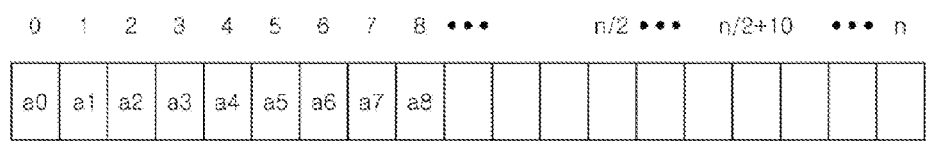
FIG. 2 is a view for describing a concept in which voice signals are converted into voice frames by a voice input unit included in the alcohol consumption determination terminal according to an embodiment of the present invention.

FIG. 2 is a view for describing a concept in which voice signals are converted into voice frames by a voice input unit included in the alcohol consumption determination terminal according to an embodiment of the present invention.

Typically, analog voice signals are sampled at a rate of 8000 per second and in the size of 16 bits (65535 steps) and converted into voice data.

The voice input unit 110 may convert received voice signals into voice data and convert the voice data into voice frame data in units of frames. Here, one piece of the voice frame data has 256 energy values.

As shown in FIG. 2, the voice data is composed of a plurality of voice frames (n=the number of frames, n=1, 2, 3, . . . ) according to an input voice.

The voice input unit 110 generates a voice frame and then sends information regarding the voice frame to the voiced/unvoiced sound analysis unit 120.

Figure 3:
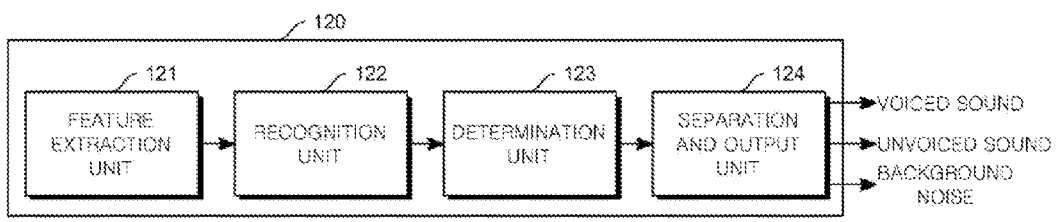
FIG. 3 is a control block diagram of a voiced/unvoiced sound analysis unit included in the alcohol consumption determination terminal according to an embodiment of the present invention.

FIG. 3 is a control block diagram of a voiced/unvoiced sound analysis unit included in the alcohol consumption determination terminal according to an embodiment of the present invention.

The voiced/unvoiced sound analysis unit 120 may include a feature extraction unit 121 configured to receive a voice frame and extract predetermined features from the voice frame, a recognition unit 122 configured to yield a recognition result for the voice frame, a determination unit 123 configured to determine whether the received voice frame is associated with a voiced sound or an unvoiced sound or whether the received voice frame is caused by background noise, and a separation and output unit 124 configured to separate and output the voice frame according to a result of the determination.

When the voice frame is received through the voice input unit 110, the feature extraction unit 121 may extract features such as periodic characteristics of harmonics or root mean square energy (RMSE) or zero-crossing count (ZC) of a low-band voice signal energy area from the received voice frame.

Generally, the recognition unit 122 may be composed of a neural network. This is because the neural network is useful in analyzing non-linear problems, that is, complicated problems that cannot be solved mathematically and thus is suitable for analyzing voice signals and determining whether a corresponding voice signal is determined as a voiced signal, an unvoiced signal, or background noise according to a result of the analysis. The recognition unit 122, which is composed of such a neural network, may assign predetermined weights to the features extracted from the feature extraction unit 121 and may yield a recognition result for the voice frame through a calculation process of the neural network. Here, the recognition result refers to a value that is obtained by calculating calculation elements according to weights assigned to features of each voice frame.

The determination unit 123 may determine whether the received voice signal corresponds to a voiced sound or an unvoiced sound according to the above-described recognition result, that is, the value calculated by the recognition unit 122. The separation and output unit 124 may separate and output the voice frame as a voiced sound, an unvoiced sound, or background noise according to a result of the determination of the determination unit 123.

Meanwhile, since a voiced sound is distinctly different from a voiced sound and background noise in terms of various features, it is relatively easy to identify the voiced sound, and there are several well-known techniques for this. For example, the voiced sound has periodic characteristics in which harmonics are repeated at a certain interval while the background noise does not have the harmonics. On the other hand, the unvoiced sound has harmonics with weak periodicity. In other words, the voiced sound is characterized in that the harmonics are repeated within one frame while the unvoiced sound is characterized in that the characteristics of the voiced sound such as the harmonics are repeated every certain number of frames, that is, is shown to be weak.

Figure 4:
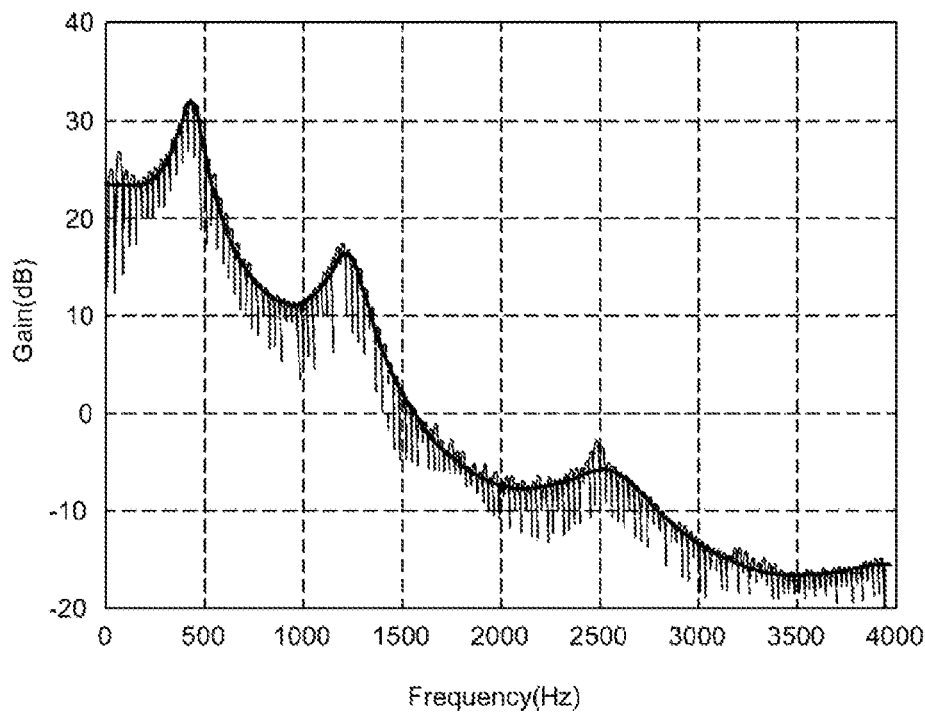
FIG. 4 is a graph showing a formant frequency extracted by a format frequency extraction unit included in the alcohol consumption determination terminal according to an embodiment of the present invention.

FIG. 4 is a graph showing a formant frequency extracted by a format frequency extraction unit included in the alcohol consumption determination terminal according to an embodiment of the present invention.

There are several methods for finding the formant frequency. Among the several methods, a method using an LPC cepstrum will be described below. However, it will be appreciated that all well-known methods are included in the present invention.

The formant frequency extraction may take a hamming window such that in order to minimize discontinuity of an input signal in order to find the LPC cepstrum.

$$X_w(n) = x(n)w(n), \quad w(n) = 0.54 - 0.46\cos\left(\frac{2\pi n}{N-1}\right), \quad 0 \leq N-1 \quad \text{[Equation 1]}$$

where N is the number of samples, and x(n) is an input signal. An AR coefficient is found by applying an autocorrelation method to the signal that takes the window, as in Equation 2. Here, p is the order.

$$r(m) = \sum_{n=0}^{N-1-m} x_w(n)x_w(n+m), \quad m = 0, 1, \ldots, p. \quad \text{[Equation 2]}$$

A filter coefficient a through an LPC analysis may be obtained by Equation 3. Here, R is a Toeplitz autocorrelation matrix.

$$Ra = r \quad \text{[Equation 3]}$$
$$r = [r(1), r(2), \ldots, r(p)]^T$$
$$a = [a_1, a_2, \ldots, a_p]^T$$
$$R = \begin{bmatrix} r(0) & r(1) & r(2) & \ldots & r(p-1) \\ r(1) & r(0) & r(1) & \ldots & r(p-2) \\ r(2) & r(1) & r(0) & \ldots & r(p-3) \\ \vdots & \vdots & \vdots & & \vdots \\ r(p-1) & r(p-2) & r(p-3) & \ldots & r(0) \end{bmatrix}$$
$$a = R^{-1}r.$$

The filter coefficient a is converted into an LPC cepstrum coefficient c by Equation 4, and m has a value up to (3/2)*p.

$$c_0 = r(0) \quad \text{[Equation 4]}$$
$$c_m = a_m + \sum_{k=1}^{m-1} \frac{k}{m} c_k a_{m-k}, \quad 1 < m < p$$
$$c_m = \sum_{k=m-p}^{m-1} \frac{k}{m} c_k a_{m-k}, \quad m > p.$$

FIG. 4 shows an amplitude spectrum and an LPC spectrum of the pronunciation of "Ah" using the above methods performed by the formant frequency extraction unit 130. Here, the thick line shows the LPC spectrum, and F1, F2, F3, F4, and F5 are found by finding peaks in the LPC spectrum, starting from the lowest frequency.

Figure 5:
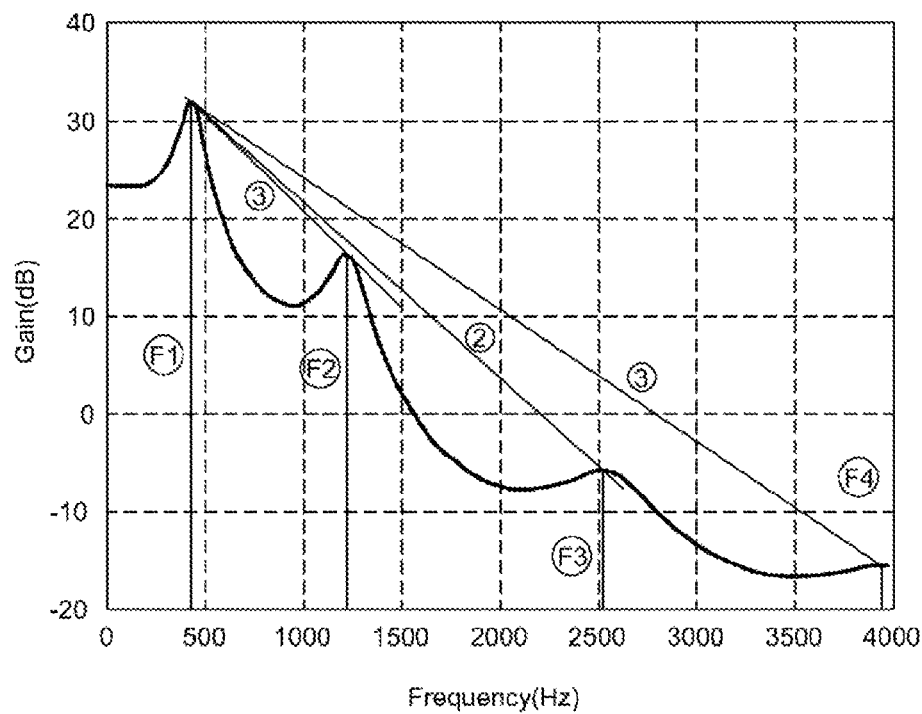
FIG. 5 is a graph for describing an operation of a formant slope extraction unit included in the alcohol consumption determination terminal according to an embodiment of the present invention.

FIG. 5 is a graph for describing an operation of a formant slope extraction unit included in the alcohol consumption determination terminal according to an embodiment of the present invention.

The formant slope extraction unit 140 may extract a formant slope using the formant frequencies extracted by the formant frequency extraction unit 130.

Referring to FIG. 5, the formant slope extraction unit 140 may extract a slope ① between the first formant frequency F1 and the fourth formant frequency F4, a slope ② between the first formant frequency F1 and the third formant frequency F3, and a slope ③ between the first formant frequency F1 and the second formant frequency F2. Here, among the plurality of formant slopes, F14 and F24 are more useful in determining whether alcohol has been consumed. A person's ability to control the volume of voice is reduced due to a change in the body after drinking. Thus, since the person cannot talk smoothly and rhythmically by using a change in energy, the person makes consecutive pronunciations with a loud voice or makes pronunciations with a loud voice even when the pronunciation should be made with a low voice. The feature denotes that a change occurs in the first formant F1. Furthermore, tongue position is changed upon pronunciation when alcohol has been consumed. This affects the second formant F2. That is, the second formant increases when the tongue is positioned forward and decreases when the tongue is positioned backward. The fourth formant F4 is not affected by an articulator, and thus is almost constant before and after drinking. Accordingly, whether alcohol has been consumed may be more easily determined according to the variations of F14 and F24.

Figure 6:
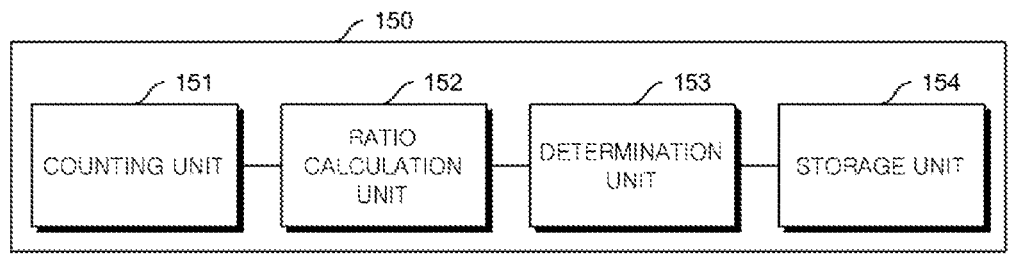
FIG. 6 is a control block diagram of an alcohol consumption determination unit included in the alcohol consumption determination terminal according to an embodiment of the present invention.
Figure 7:
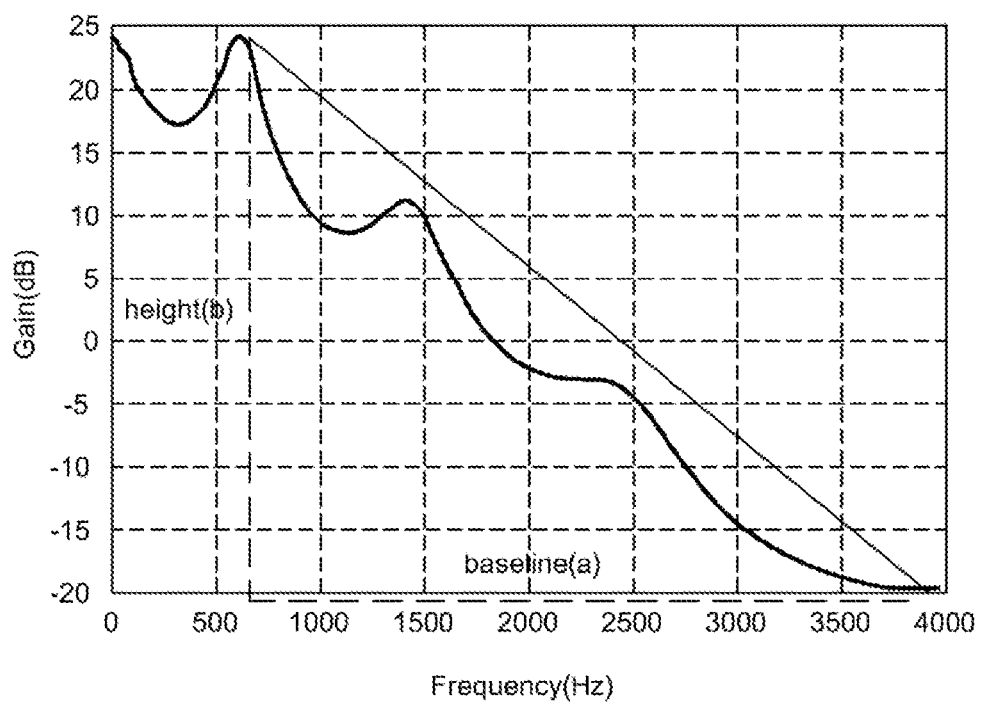
FIG. 7 is a view illustrating a slope between a first formant frequency and a fourth formant frequency in order to describe an operation of an alcohol consumption determination unit included in the alcohol consumption determination terminal according to an embodiment of the present invention.

FIG. 6 is a control block diagram of an alcohol consumption determination unit included in the alcohol consumption determination terminal according to an embodiment of the present invention, and FIG. 7 is a view illustrating a slope between a first formant frequency and a fourth formant frequency in order to describe an operation of an alcohol consumption determination unit included in the alcohol consumption determination terminal according to an embodiment of the present invention.

An alcohol consumption determination unit 150 may include a counting unit 151, a ratio calculation unit 152, a determination unit 153, and a storage unit 154.

The counting unit 151 compares, with a pre-stored threshold, a formant slope of a voice frame determined as a voiced sound in the entire section of a voice signal and counts the number of voice frames each having a formant slope smaller than the threshold.

Referring to FIG. 7, the formant slope extraction unit 140 extracts a slope between the first formant frequency and the fourth formant frequency of the voice frame. The formant slope refers to a ratio between the base a and the height b of a triangle having a hypotenuse that is a line connecting the first formant frequency and the forth formant frequency, as shown in Equation 5 below:

$$F14 = \frac{b}{a} \quad \text{[Equation 5]}$$

where a is a variation of frequency, and b is a variation of energy.

The ratio calculation unit 152 compares a result calculated by the counting unit 151 with the total number of voice frames (the total number of voice frames determined as voiced sounds) to calculate a ratio of the two. The ratio calculation unit 152 may calculate the ratio using Equation 6 below:

$$\text{Rate} = \frac{C}{T} \quad \text{[Equation 6]}$$

where C is the counted number, and T is the total number of voice frames (the total number of voice frames determined as voiced sounds).

When the ratio calculated by the ratio calculation unit 152 is greater than a value that is pre-stored in the storage unit 154, the determination unit 153 determines that alcohol has been consumed.

Figure 8:
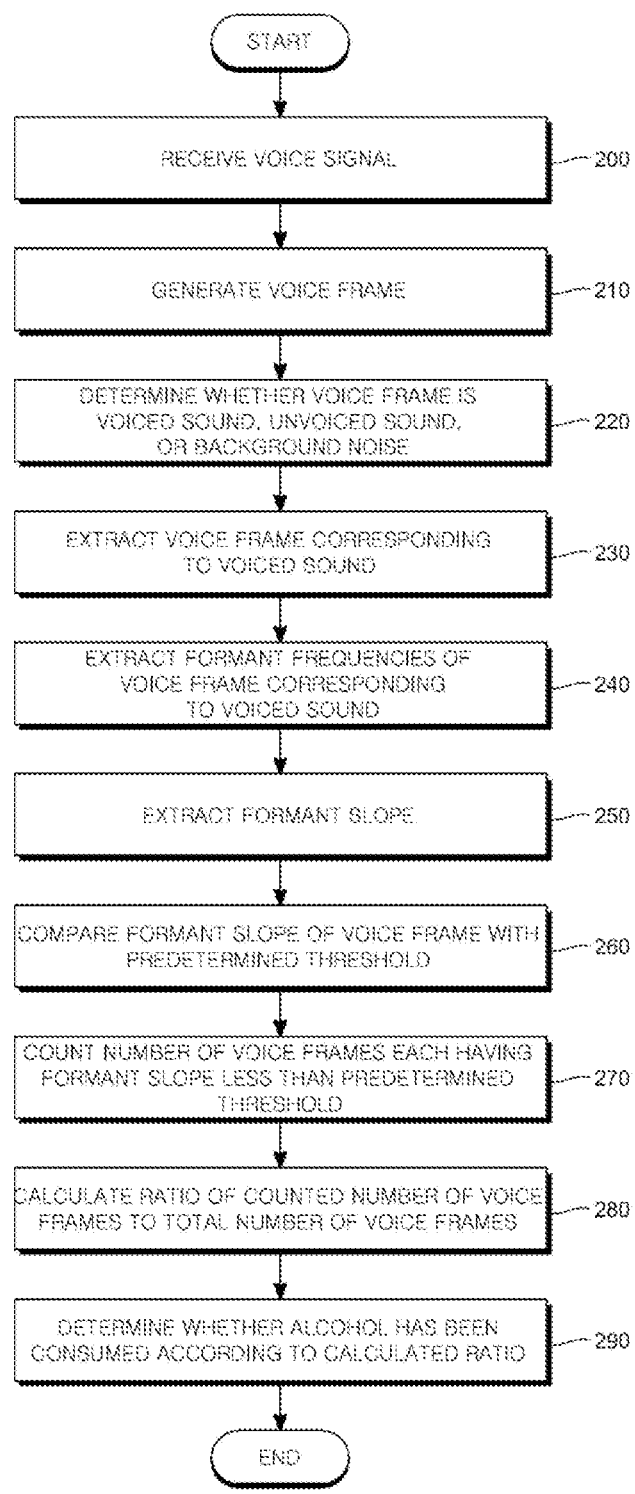
FIG. 8 is a control flowchart showing an alcohol consumption determination method according to an embodiment of the present invention.

FIG. 8 is a control flowchart showing an alcohol consumption determination method according to an embodiment of the present invention.

The voice input unit 110 may receive a person's voice, convert the received voice into voice data, convert the voice data into voice frames in units of frames, and output the voice frames. The voice input unit 110 may convert voice signals into the frequency domain using a transform method such as Fast Fourier Transform (FFT) (200 and 210).

The voiced/unvoiced sound analysis unit 120 may receive a voice frame, extract predetermined features from the voice frame, and analyze whether the voice frame is associated with a voiced sound, an unvoiced sound, or background noise according to the extracted features (220).

The voiced/unvoiced sound analysis unit 120 may determine whether the voice frame corresponds to a voiced sound or an unvoiced sound according to a recognition result obtained by the above method. The voiced/unvoiced sound analysis unit 120 may extract and output the voice frame corresponding to the voiced sound according to a result of the determination (230).

The formant frequency extraction unit 130 may extract formant frequencies for the voice frame determined as the voice sound through the voiced/unvoiced sound analysis unit 120. The formant frequencies are called F1, F2, F3, F4, and F5 in ascending order of harmonics in a frequency intensity distribution (240).

The formant slope extraction unit 140 finds a formant slope using the formant frequencies extracted by the formant frequency extraction unit 130. The formant slope is a slope of a straight line connecting one formant frequency and another. For example, a slope of a straight line connecting a first formant frequency F1 and a fourth formant frequency F4 may be defined as a formant slope F14 (250).

The alcohol consumption determination unit 150 may determine whether alcohol has been consumed using the formant slope. The alcohol consumption determination unit 150 may compare the formant slope of the voice frame determined as the voiced sound with a threshold and may determine that alcohol has been consumed when a ratio of the number of voice frames that are determined as having formant slopes smaller than the threshold to the total number of voice frames (the total number of voice frames determined as voiced sounds) is greater than or equal to a certain value (260, 270, 280, and 290).

Although the present invention has been described with reference to exemplary embodiments thereof, it should be understood that numerous other modifications and variations can be made without departing from the spirit and scope of the present invention by those skilled in the art. It is obvious that the modifications and variations fall within the spirit and scope thereof.

The invention claimed is:

1. A computer implemented method for determining whether alcohol is consumed by a person in a vehicle, the computer implemented method comprising:
   receiving a voice signal from said person and converting the received voice signal into a plurality of voice frames;
   extracting a voice frame corresponding to a voiced sound among the plurality of voice frames;
   extracting a plurality of formant frequencies of the voice frame corresponding to the voiced sound;
   calculating a formant slope between two formant frequencies among the plurality of formant frequencies;
   determining whether alcohol is consumed by said person according to the calculated formant slope, wherein the determining comprises:
      counting the number of voice frames each having a formant slope less than a predetermined threshold,
      computing a ratio of the counted number of voice frames to the total number of voice frames, and determining whether alcohol is consumed by said person when the computed ratio is greater than a predetermined value; and enabling or disabling the vehicle based on the determination whether alcohol is consumed by said person.

2. The computer implemented method of claim 1, wherein the extracting a voice frame corresponding to a voiced sound among the plurality of voice frames comprises:

extracting predetermined features from a voice frame among the plurality of voice frames, and determining whether said voice frame is from a voiced sound, an unvoiced sound, or background noise.

3. The computer implemented method of claim 2, wherein the predetermined features comprise periodic characteristics of harmonics, root mean square energy (RMSE), or zero-crossing count (ZC) of a low-band voice signal energy area.

4. The computer implemented method of claim 2, wherein the determining whether said voice frame is from a voiced sound, an unvoiced sound, or background noise comprises using neural network.

5. The computer implemented method of claim 1, wherein the extracting of a plurality of formant frequencies of the voice frame corresponding to the voiced sound comprises using algorithms of finding the formant frequency.

6. The computer implemented method of claim 5, wherein one of the algorithms of finding the formant frequency uses a linear prediction coefficient (LPC) cepstrum.

7. The computer implemented method of claim 1, wherein the extracting of a plurality of formant frequencies of the voice frame corresponding to the voiced sound comprises extracting first to fourth formant frequencies of the voice frame.

8. The computer implemented method of claim 1, wherein the calculating a formant slope between two formant frequencies among the plurality of formant frequencies comprises calculating a formant slope between the first formant frequency and the fourth formant frequency.

9. The computer implemented method of claim 1, wherein the calculating a formant slope between two formant frequencies among the plurality of formant frequencies comprises calculating a formant slope between the second formant frequency and the fourth formant frequency.

10. A non-transitory computer-readable recording medium having a computer program recorded thereon for performing a method for determining whether alcohol is consumed by a person in a vehicle, the method comprising:

receiving a voice signal from the person in the vehicle and converting the received voice signal into a plurality of voice frames;

extracting a voice frame corresponding to a voiced sound among the plurality of voice frames;

extracting a plurality of formant frequencies of the voice frame corresponding to the voiced sound;

calculating a formant slope between two formant frequencies among the plurality of formant frequencies;

determining whether alcohol is consumed by the person according to the calculated formant slope, wherein the determining comprises:

counting the number of voice frames each having a formant slope less than a predetermined threshold, computing a ratio of the counted number of voice frames to the total number of voice frames, and determining whether alcohol is consumed by the person when the computed ratio is greater than a predetermined value; and enabling or disabling the vehicle based on the determination whether alcohol is consumed by the person.

11. The non-transitory computer-readable recording medium of claim 10, wherein the extracting a voice frame corresponding to a voiced sound among the plurality of voice frames comprises:

extracting predetermined features from a voice frame among the plurality of voice frames, and determining whether said voice frame is from a voiced sound, an unvoiced sound, or background noise.

12. The non-transitory computer-readable recording medium of claim 11, wherein the predetermined features comprise periodic characteristics of harmonics, root mean square energy (RMSE), or zero-crossing count (ZC) of a low-band voice signal energy area.

13. The non-transitory computer-readable recording medium of claim 11, wherein the determining whether said voice frame is from a voiced sound, an unvoiced sound, or background noise comprises using neural network.

14. The non-transitory computer-readable recording medium of claim 10, wherein the extracting of a plurality of formant frequencies of the voice frame corresponding to the voiced sound comprises using algorithms of finding the formant frequency.

15. The non-transitory computer-readable recording medium of claim 14, wherein one of the algorithms of finding the formant frequency uses a linear prediction coefficient (LPC) cepstrum.

16. The non-transitory computer-readable recording medium of claim 10, wherein the extracting of a plurality of formant frequencies of the voice frame corresponding to the voiced sound comprises extracting first to fourth formant frequencies of the voice frame.

17. The non-transitory computer-readable recording medium of claim 10, wherein the calculating a formant slope between two formant frequencies among the plurality of formant frequencies comprises calculating a formant slope between the first formant frequency and the fourth formant frequency.

18. The non-transitory computer-readable recording medium of claim 10, wherein the calculating a formant slope between two formant frequencies among the plurality of formant frequencies comprises calculating a formant slope between the second formant frequency and the fourth formant frequency.

* * * * *